(12) United States Patent
Chuang

(10) Patent No.: US 9,389,261 B2
(45) Date of Patent: Jul. 12, 2016

(54) SYSTEMS FOR MEASURING ELECTRIC RESISTANCE AND RELATION BETWEEN APPLIED PRESSURE AND STREAMING POTENTIAL ACROSS THE MEMBRANE AND UTILITY THEREOF

(71) Applicant: CHUNG YUAN CHRISTIAN UNIVERSITY, Tao-Yuan (TW)

(72) Inventor: Ching-Jung Chuang, Tao-Yuan (TW)

(73) Assignee: CHUNG YUAN CHRISTIAN UNIVERSITY, Tao-Yuan (TW)

(*) Notice: Subject to any disclaimer, the term of this patent is extended or adjusted under 35 U.S.C. 154(b) by 228 days.

(21) Appl. No.: 14/465,903

(22) Filed: Aug. 22, 2014

(65) Prior Publication Data

US 2014/0361797 A1 Dec. 11, 2014

Related U.S. Application Data

(62) Division of application No. 13/193,982, filed on Jul. 29, 2011, now Pat. No. 8,849,600.

(30) Foreign Application Priority Data

Jan. 28, 2011 (TW) .............................. 100103254 A

(51) Int. Cl.
*G01R 29/24* (2006.01)
*B01D 61/42* (2006.01)
*B01D 65/10* (2006.01)
*G01N 15/08* (2006.01)

(52) U.S. Cl.
CPC .............. *G01R 29/24* (2013.01); *B01D 61/427* (2013.01); *B01D 65/10* (2013.01); *G01N 15/08* (2013.01); *B01D 2325/26* (2013.01)

(58) Field of Classification Search
CPC combination set(s) only.
See application file for complete search history.

(56) References Cited

U.S. PATENT DOCUMENTS

| 5,475,319 A | 12/1995 | Hirae et al. |
| 8,849,600 B2 * | 9/2014 | Chuang ................ B01D 61/427 702/65 |

FOREIGN PATENT DOCUMENTS

| TW | I237696 | 8/2005 |
| TW | I381182 | 1/2013 |

* cited by examiner

*Primary Examiner* — Walter L Lindsay, Jr.
*Assistant Examiner* — Jas Sanghera
(74) *Attorney, Agent, or Firm* — WPAT, PC; Justin King

(57) ABSTRACT

The present invention provides a method for measuring net charge density of membrane and apparatus thereof. The method measures the net charge density of a membrane by utilizing the relation between the mechanical pressure difference applied across the membrane and the generated streaming potential or the relation between the applied electric field and the generated electroosmotic flow. The present invention also provides a method and an apparatus for measuring the resistance of a membrane.

7 Claims, 4 Drawing Sheets

SYSTEMS FOR MEASURING ELECTRIC RESISTANCE AND RELATION BETWEEN APPLIED PRESSURE AND STREAMING POTENTIAL ACROSS THE MEMBRANE AND UTILITY THEREOF

CROSS REFERENCE TO RELATED APPLICATIONS

This is a divisional of U.S. Ser. No. 13/193,982, filed Jul. 29, 2011 by the same inventors, and claims priority there from. This divisional application contains rewritten claims to the restricted-out subject matter of original claims.

BACKGROUND OF THE INVENTION

1. Field of the Invention

The present invention is generally related to a method for measuring a net charge density of a membrane and an apparatus thereof, and more particularly to a method for measuring a net charge density of a porous membrane such as a microfiltration, ultrafiltration or nanofiltration membrane and an apparatus thereof.

2. Description of the Prior Art

The characteristic parameters of a membrane generally can be categorized into performance parameters, morphology parameter, and charge parameters. In the charge parameters, the zeta potential of a membrane usually is measured by the streaming potential method or electroosmosis method and its influence to the filtration performance of the membrane is analyzed but the net charge density inside the membrane is usually uncertain.

Particularly, regarding nanofiltration (NF) membranes, the key of the species rejection mechanism of a nanofiltration (NF) membrane is the electrostatic repulsion between species and the NF membrane. The electrostatic repulsion force is an important factor in controlling the filtration performance. The charge parameters used to evaluate the filtration performance of the NF membrane and the ion exchange membrane are usually estimated from the net charge density per unit volume or area of a membrane. According to the prior art, the value of the net charge density of a NF membrane per unit volume is usually acquired by the estimation from the experimental result accompanying with the theoretical simulation. Since most of the NF membranes are composite membranes, the pore diameter is very small and thus overlapping of electric double layers is very serious to thereby cause the difficulty in measuring the real zeta potential of the surfaces of the pore walls of the NF membrane.

Regarding the estimation of the net charge density per unit volume, Ta-Shung et al. (Tai-Shung, C., J. Lv and W. Kai Yu, "Investigation of amphoteric polybenzimidazole (PBI) nanofiltration hollow fiber membrane for both cation and anions removal", *J. Membrane Sci.*, 310, 557-566 (2008)) use Speigler-Kedem model (SKM) together with Teorell-Meyer-Sievers model (TMS) to estimate the net charge density per unit volume for PBI nanofiltration (NF) membrane. SKM is used to describe the relation between solution flux and solute flux while TMS is used to describe the relation of ion permeation. Such a method accompanying with the result of the experimental blocking rate calculates the reflection coefficient of the membrane to thereby estimate the charge quantity of the membrane per unit volume. The result indicates that the effective net charge density per unit volume of the membrane increases with the increase of the ionic concentration.

On the other hand, Bandini et al. (Bandini, S., D. Jennifer and V. Daniele, "The role of pH and concentration on the ion rejection in polyamide nanofiltration membranes", *J. Membrane Sci.*, 264, 65-74 (2005)) use DSPM-DE (Donnan Steric Pore Model (DSPM) and Dielectric Exclusion) to estimate the net charge density per unit volume for the DK02 nanofiltration (NF) membrane (OSMONICS). The experiment of filtration of a sodium chloride aqueous solution is performed and the blocking rate obtained from the experiment accompanying with the theoretical model and the charge neutrality balance condition is used to estimate the net charge density per unit volume. The result shows that the charge density increases with the increase of the concentration of salts. The same result is obtained even for different pH values. Then, Bandini et al. (Bandini, S. and C. Mazzoni, "On nanofiltration Desal-5 DK performances with calcium chloride-water solutions", *Separation and Purification Technology*, 52, 232-240 (2006)) also use DK02 nanofiltration (NF) membranes in the $CaCl_2$ circulating sweeping filtration experiment and then the volumetric net charge density of the NF membrane is estimated from the ion blocking experimental result. The estimation result indicates that the electrical potential of the membrane is increased by ion adsorption and due to the competition between the adsorption of calcium ions and the adsorption of chloride ions when the concentration is increased to a threshold level the isoelectric point of volumetric charges of the membrane appears at two different concentrations.

Therefore, when, according to the prior art, the method of utilizing the experimental result of the ion blocking rate together with the theoretical model is applied to simulate the net charge density, the charge density is increased with the increase of the concentration of ions. In addition, it is found that larger deviation in estimation will appear if different methods are used based on various ionic radii defined. Thus, it is important to effectively measure a net charge density per unit volume and a more reliable measurement method is required.

SUMMARY OF THE INVENTION

In light of the above background, in order to fulfill the industrial requirements, the invention provides a method for measuring a net charge density of a membrane and an apparatus thereof.

One object of the present invention is to provide a method for measuring a net charge density of a membrane and an apparatus thereof to measure the net charge density of a porous membrane such as a microfiltration (MF), ultrafiltration (UF) or nanofiltration (NF) membrane.

One object of the present invention is to provide a method for measuring a net charge density of a membrane and an apparatus thereof to utilize the equilibrium condition between the applied mechanical pressure difference and the electroosmotic flow of the membrane to acquire the net charge density of the membrane per unit volume.

One object of the present invention is to provide a method for measuring a net charge density of a membrane and an apparatus thereof to use the relation of the applied mechanical pressure difference and the streaming potential of the membrane to acquire the net charge density per unit volume of the membrane.

One object of the present invention is to provide a method for measuring electric resistance of a membrane and an apparatus thereof to measure the resistance of a porous membrane such as a microfiltration (MF), ultrafiltration (UF) or nanofiltration (NF) membrane. Furthermore, if the porosity of the membrane is known to be $\in$ (for example, when a membrane has large pores, the porosity $\in$ can be obtained from other methods), the average electrical conductivity $k_m$ of the membrane can be acquired according to the method and apparatus for measuring electric resistance of a membrane disclosed by the invention. On the other hand, if the average electrical conductivity $k_m$ of the membrane is known, the porosity $\in$ can be acquired according to the method and apparatus for measuring electric resistance of a membrane disclosed by the invention.

Accordingly, one embodiment of the invention provides a method for measuring a net charge density of a membrane. The method comprises the following steps. At first, a membrane to be measured is provided. A solution is provided and infiltrates the membrane. Then, a mechanical pressure difference $\Delta P$ is applied across the membrane to generate permeate flow as well as streaming potential. The net charge density $\rho_E$ of the membrane per unit volume is acquired according to the relation of the mechanical pressure difference $\Delta P$ and the streaming potential $E$ by the following equation (7): $\rho_E = -(E/\Delta P)*(\mu \in k_m / K_p)$ where $\in k_m$ represents the product of the porosity $\in$ and average electrical conductivity $k_m$ of the membrane, $\mu$ represents viscosity of the solution, and $K_p$ represents permeability. Or, after applying a mechanical pressure difference $\Delta P$, an electric field is applied across the membrane to generate osmotic flow. The net charge density $\rho_E$ of the membrane per unit volume is then calculated according to the relation between the electric field E and the mechanical pressure difference $\Delta P$ or between the osmotic flow and the current applied.

In one embodiment, in the above method, $\rho_E$ represents the net charge density of the membrane per unit volume can be acquired by the following equation (9): $\rho_E = -(Q_p/I_a)*(\mu \in k_m / K_p)$ where $\in k_m$ represents the product of the porosity $\in$ and average electrical conductivity $k_m$ of the membrane, $\mu$ represents viscosity of the solution, $K_p$ represents permeability obtained from the permeate flow, $I_a$ represents the current induced by the electric field, and $Q_p$ represents the electroosmotic volumetric flow rate of the osmotic flow. On the other hand, when a mechanical pressure difference $\Delta P$ is applied to generate the first permeate flow, the streaming potential $E$ between the two surfaces of the membrane is measured at the same time. The net charge density $\rho_E$ of the membrane per unit volume can be acquired by the equation (7): $\rho_E = -(E/\Delta P)*(\mu \in k_m / K_p)$.

In one embodiment, in the above method, the product of the porosity $\in$ and average electrical conductivity $k_m$ of the membrane is acquired by measuring electric resistance of the membrane.

In one embodiment, the method of measuring electric resistance of the membrane comprises: providing a solution; having the solution infiltrate the membrane; disposing the membrane between two electrodes and filling the solution between the membrane and each electrode; and measuring the relation of current and voltage between the two electrodes while the target membrane is installed in between or is not installed and calculating the resistance of the membrane according to Ohm's law.

In one embodiment, in the above method, the membrane to be measured is selected from the group consisting of the following: porous membrane, microfiltration membrane, ultrafiltration membrane, nanofiltration membrane, and ion exchange membrane.

In one embodiment, in the above method, a predetermined mechanical pressure difference is used to generate permeate flow and the electric field strength is adjusted to have the electroosmotic flow be equal to the permeate flow in magnitude but be opposite in direction. That is, the electric field strength is adjusted to have the first permeate flow generated by the mechanical pressure difference stop to thereby calculate the net charge density $\rho_E$ of the membrane per unit volume. In the above method, on the other hand, the mechanical pressure difference $\Delta P$ is applied and the streaming potential $E$ between the two surfaces of the membrane is measured at the same time so that the streaming potential coefficient ($E/\Delta P$) can be used to calculate the net charge density $\rho_E$.

In one embodiment, the membrane to be measured is a porous membrane including microfiltration membrane, ultrafiltration membrane, nanofiltration membrane, or ion exchange membrane.

In one embodiment, the method for measuring the streaming potential uses a high impedance voltmeter to measure the potential difference across the membrane.

Another embodiment of the invention provides an apparatus for measuring a net charge density of a membrane, comprising: a membrane permeation measurement module, a pressure measurement module, and a streaming potential measurement module. The membrane permeation measurement module comprises a chamber, two electrodes disposed in the chamber, a membrane to be measured, and a liquid, for measuring permeation rate caused by a mechanical pressure difference between two surfaces of the membrane and electroosmotic volumetric flow rate caused by an electric field applying on the two surfaces of the membrane. The pressure measurement module measures the mechanical pressure difference between the two surfaces of the membrane. The streaming potential measurement module measures the streaming potential of the membrane.

In one embodiment, the apparatus further comprises a membrane electric resistance measurement module, for measuring electric resistance of the membrane.

In one embodiment, the membrane permeation measurement module further comprises: a temperature controller, for controlling the chamber at a fixed temperature; a pump, for transporting the solution into the chamber; an electronic balance, for measuring a flow quantity of the liquid flowing through the membrane and outputting the flow quantity; and a power supply, electrically coupled to the two electrodes of the membrane permeation measurement module.

In one embodiment, the pressure measurement module comprises: a pressure valve, for controlling and applying a pressure on the two surfaces of the membrane to generate a mechanical pressure difference $\Delta P$ across the membrane; and a pressure sensor, for measuring the mechanical pressure difference $\Delta P$ and outputting the mechanical pressure difference $\Delta P$.

In one embodiment, the streaming potential measurement module comprises: a high impedance voltmeter, for measuring voltage between the two electrodes when the liquid passes through the membrane and outputting the voltage.

In one embodiment, the membrane electric resistance measurement module comprises: a membrane resistance measurement container; two plate-electrodes, disposed in the membrane resistance measurement container and having a specific distance between the two electrode plates; a solution, filled in the membrane resistance measurement container; an AC power supply, for supplying power between the two electrode plates; two voltmeter, one of which is electrically coupled to the two electrode plates and the other of which has one end electrically coupled to the AC power supply and has the other end electrically coupled to one of the two electrode plates to measure voltages and currents; wherein under a specific voltage the variation of currents between the two electrodes is measured while the membrane is installed in between or is not installed and then the electric resistance of the membrane is calculated from the above relation of current variation based on Ohm's law.

Another embodiment of the invention provides an apparatus for measuring electric resistance of a membrane by having the above membrane resistance measurement module become a stand-alone apparatus.

Another embodiment of the invention provides a method for measuring electric resistance of a membrane, comprising: providing a solution; having the solution infiltrate the membrane; disposing the membrane between two electrodes and filling the solution between the membrane and each electrode; and measuring the relation of current and voltage between the two electrodes while the membrane is installed in between or is not installed and calculating the electric resistance of the membrane according to Ohm's law.

In conclusion, the present invention discloses a method for measuring a net charge density of a membrane and the apparatus thereof to utilize the applied mechanical pressure difference and the streaming potential of the membrane or the applied electric field and the electroosmotic volumetric flow rate of the electroosmotic flow to acquire the net charge density inside the membrane so that the net charge density per unit volume can be measured effectively to solve the problem in the prior art.

DESCRIPTION OF THE PREFERRED EMBODIMENTS

The invention discloses a method for measuring a net charge density of a membrane and the apparatus thereof as well as a method and an apparatus for measuring electric resistance of a membrane. Detail descriptions of the steps and elements will be provided in the following in order to make the invention thoroughly understood. Obviously, the application of the invention is not confined to specific details familiar to those who are skilled in the art. On the other hand, the common steps and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Figure 1:
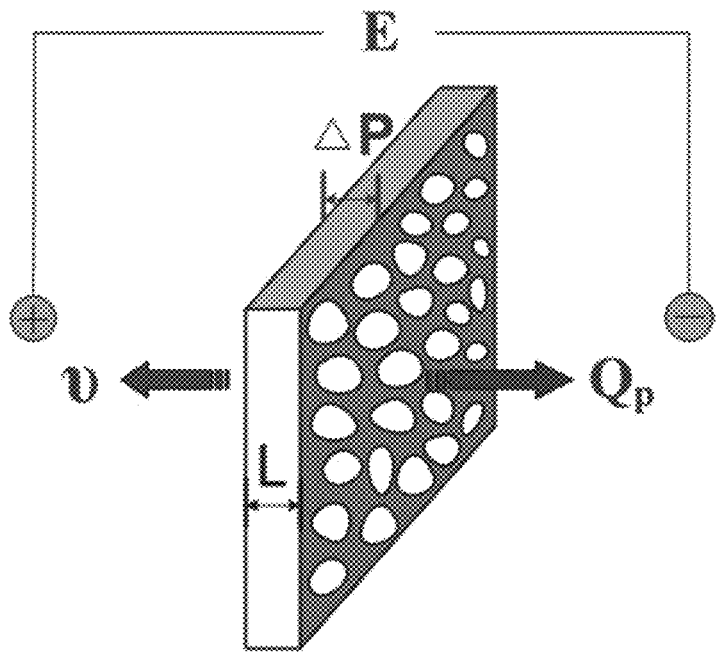
FIG. 1 shows a schematic diagram illustrating a membrane being soaked in a solution and applied with a mechanic pressure and an electric field according to one embodiment of the invention.

The method for measuring a net charge density of a membrane of the present invention utilizes the balance condition of the applied mechanical pressure difference and the electroosmotic flow or the relation of the applied mechanical pressure difference and the streaming potential to obtain the net charge density of a membrane per unit volume. The so called "balance condition of the applied mechanical pressure difference and the electroosmotic flow" means that for the pore of the membrane in a solution experience an electric force and a mechanical pressure where the electric force is equal to mechanical pressure. That is, a mechanical pressure difference $\Delta P$ is applied on the two sides (two surfaces) of the membrane to generate permeate flow and then an electric field is applied to generate electroosmotic flow to have the magnitude equal to the permeate flow but opposite in direction so that the net charge density of the membrane can be obtained from the relation of the electric field and the mechanical pressure difference $\Delta P$. Or, the mechanical pressure difference $\Delta P$ and the electric field can be applied separately and the condition of the magnitude of permeated flow by the mechanical pressure difference $\Delta P$ is the same as the electroosmotic flow induced by an electric field is then selected to acquire the net charge density of the membrane. FIG. 1 shows a schematic diagram illustrating a membrane being soaked in a solution and applied with a mechanical pressure and an electric field according to one embodiment of the invention where E represents the applied electric field, L represents the thickness of the membrane, $\Delta P$ represents the applied mechanical pressure difference, $Q_p$ represents the electroosmotic volumetric flow rate of the electroosmotic flow, and $\upsilon$ represents the superficial velocity.

Specifically, assuming the thickness (L), porosity ($\in$), and cross-sectional area (A) of a membrane are known, as shown in FIG. 1, when DC (direct current) electric field strength (E) is applied across the membrane, the solution in the pores of the membrane experiences a force caused by the electric field, shown by the following equation (1):

$$F_e = \rho'_E \times A \times L \times \in \times E \qquad (1)$$

where $\rho'_E$ is the net charge of the solution per unit volume in the pores and the net charge density $\rho_E$ of the membrane per unit volume can be represented by $\rho_E = -\rho'_E$ based on the assumption of electrical neutrality of the whole membrane.

If a mechanical pressure difference is applied on the two surfaces of the membrane instead, the solution in the pores of the membrane experiences a force caused by the mechanical pressure difference, shown by the following equation (2):

$$F_P = \Delta P \times A \times \in \qquad (2)$$

where $\Delta P$ represents the applied mechanical pressure difference.

An electric field is applied to generate electroosmotic flow of the solution in the pores while a mechanical pressure difference is applied to generate permeate flow. When the electroosmotic flow is equal to the permeate flow, that is, the two forces are the same (equation (1)=equation (2)), the following equation (3) is obtained:

$$\frac{\Delta P}{L} = \rho'_E \times E. \tag{3}$$

A liquid flowing in a porous body can be represented by Darcy's law, shown in the following equation (4):

$$\frac{\Delta P}{L} = \frac{\mu \upsilon}{K_P} \tag{4}$$

where $K_p$ represents permeability and u represents the superficial velocity.

The following equation (5) can be obtained from the equations (3) and (4):

$$\rho'_E = \frac{\mu \upsilon}{K_P E} \tag{5}$$

Besides, by using the relation of the electric field strength and the current, that is, the equation (6):

$$E = \frac{I}{k_m A \varepsilon} \tag{6}$$

the following equation (7) can be obtained:

$$\rho'_E = \frac{\mu k_m \varepsilon}{K_P} \left( \frac{Q_P}{I_a} \right) \tag{7}$$

where $k_m$ represents the average electrical conductivity of the solution in the porous body, $Q_p$ represents the electroosmotic volumetric flow rate ($= \upsilon A$), and $I_a$ represents the electric current.

Then, according to Onsager principle, the relation of the electroosmotic flow and the streaming potential $\overline{E}$ is shown by the following equation (8):

$$\frac{\overline{E}}{\Delta P} = \frac{Q_P}{I}. \tag{8}$$

Therefore, the net charge of the solution per unit volume in the pores $\rho'_E$ can be represented by the following equation (9):

$$\rho'_E = \frac{\mu k_m \varepsilon}{K_P} \left( \frac{\overline{E}}{\Delta P} \right) \tag{9}$$

where $\overline{E}$ represents the streaming potential and $\Delta P$ represents the applied mechanical pressure difference. According to the method of the invention, base on the equation (7), the relation of the measured electroosmotic volumetric flow rate of the membrane and the applied current can be used to acquire the net charge density. Besides, based on the equation (9), the relation of the measured streaming potential and the mechanical pressure difference can be used to acquire the net charge density.

In the above equations (7) and (9), the average electrical conductivity $k_m$ of the solution in the pores should be obtained while the net charge density is to be determined. Since the overlapping of electric double layers becomes obvious accompanying with the decrease of the pore diameter of the membrane, there is serious deviation if the conductivity $k_b$ of the bulk solution is used to estimate the net charge density. Thus, the method for measuring a net charge density of a membrane of the present invention also provides a method for measuring electric resistance of the membrane and the conductivity of the solution in the pores is obtained from the data of the electric resistance of the membrane.

Figure 2:
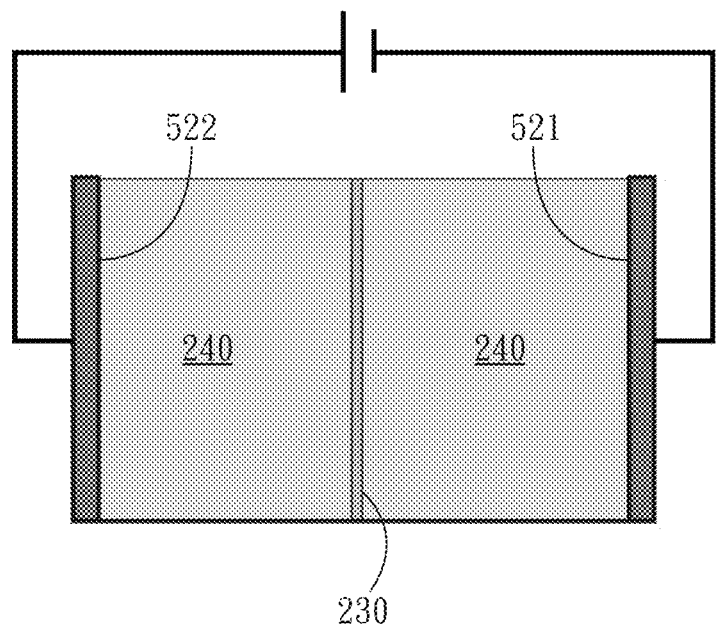
FIG. 2 shows a schematic diagram illustrating a membrane electric resistance measurement module according to one embodiment of the invention.

FIG. 2 shows a schematic diagram illustrating a membrane electric resistance measurement module. The membrane to be measured is soaked in the solution and a voltage is applied between the two electrodes. The sum of the resistance $R_s$ of the solution and the resistance $R_m$ of the membrane is $R_1$, that is, $R_1 = R_s + R_m$. If the membrane material is non-electrically-conductive, when the thickness of the membrane is L, the cross-sectional area is A, the porosity is $\in$, the relation of $R_m$ and the average conductivity $k_m$ of the solution in the pores is $$R_m = \frac{L}{A \varepsilon k_m}.$$

The following equation (10) can be obtained when $$R_m = \frac{L}{A \varepsilon k_m}$$

is inserted into the equation of $R_1$:

$$R_1 = R_s + \frac{L}{A \varepsilon k_m}. \tag{10}$$

In the same module, after the membrane is taken out, the resistance $R_2$ is measured and the following equation (11) is obtained:

$$R_2 = R_s + \frac{L}{A k_b} \tag{11}$$

where $k_b$ represents the conductivity of the bulk solution contacting the membrane surface. The resistance difference $\Delta R (= R_1 - R_2)$ with or without the membrane in the solution is obtained from subtracting $R_2$ from $R_1$ and then the following equation (12) is obtained by rearrangement:

$$\frac{k_b}{\varepsilon k_m} = 1 + \frac{A k_b \Delta R}{L}. \tag{12}$$

For micro-pores, unless the ionic strength of the solution is very high, $k_b$ is not equal to $k_m$ ($k_b \neq k_m$). The above equation (12) can be used to acquire the product ($\in k_m$) of the porosity $\in$ and average electrical conductivity $k_m$ of the membrane.

According to one embodiment of the invention, the method for measuring a net charge density of a membrane is disclosed. The method comprises the following steps. At first, a membrane to be measured is provided where the product ($\in k_m$) of the porosity E and average electrical conductivity $k_m$ of the membrane is known and can be obtained from the above equation (12) by the apparatus shown in FIG. 2. A solution is provided and infiltrates the membrane. Then, a mechanical pressure difference ΔP is applied between two surfaces of the membrane (substantially the two ends of the pore in the membrane) to generate permeate flow. After applying a mechanical pressure difference ΔP, an electric field is applied on the two surfaces of the membrane to generate electroosmotic flow. The net charge density $\rho_E$ of the membrane per unit volume is then acquired according to the relation between the electric field E and the mechanical pressure difference ΔP or between the electroosmotic flow and the current when the permeate flow is equal to the electroosmotic flow. That is, the net charge density $\rho_E$ of the membrane per unit volume can be calculated by the following equation (9): $\rho_E = -(Q_p/I_a)*(\mu \in k_m/K_p)$ where $\in k_m$ represents the product of the porosity $\in$ and average electrical conductivity $k_m$ of the membrane, μ represents viscosity of the solution, $K_p$ represents permeability obtained from the permeate flow, $I_a$ represents the current caused by the electric field, and $Q_p$ represents the volumetric flow rate of the electroosmotic flow.

In the above method, the procedure of applying the mechanical pressure difference and the procedure of applying the electric field can be performed separately to measure the permeate flow at different mechanical pressure differences and the electroosmotic flow at different electric field strength separately. From the permeate flows and the electroosmotic flows generated by the two procedures respectively, the mechanical pressure difference ΔP and the electric field E at the time the permeate flow is equal to the electroosmotic flow are selected to calculate the net charge density $\rho_E$ of the membrane per unit volume. On the other hand, the procedure of applying the mechanical pressure difference and the procedure of applying the electric field can be performed at the same time. A predetermined mechanical pressure difference is used to generate permeate flow and the electric field strength is adjusted to have the electroosmotic flow be equal to the permeate flow in magnitude but opposite in direction. That is, the electric field strength is adjusted to have the permeate flow generated by the mechanical pressure difference stop and then the mechanical pressure difference ΔP and the electric field E at the time are used to obtain the net charge density $\rho_E$ of the membrane per unit volume.

According to another embodiment of the invention, the method for measuring a net charge density of a membrane is disclosed. The method comprises the following steps. At first, a membrane to be measured is provided where the product ($\in k_m$) of the porosity E and average electrical conductivity $k_m$ of the membrane is known and can be obtained from the above equation (12) by the apparatus shown in FIG. 2. A solution is provided and infiltrates the membrane. Then, a mechanical pressure difference ΔP is applied between two surfaces of the membrane (substantially the two ends of the pore in the membrane) to generate permeate flow as well as streaming potential. The net charge density $\rho_E$ of the membrane per unit volume is calculated according to the relation of the mechanical pressure difference ΔP and the streaming potential $\overline{E}$ by the following equation (7): $\rho_E = -(\overline{E}/\Delta P)*(\mu \in k_m/K_p)$ where $\in k_m$ represents the product of the porosity $\in$ and average electrical conductivity $k_m$ of solution in the membrane pore, μ represents viscosity of the solution, and $K_p$ represents permeability.

In one embodiment, the method for measuring the resistance of the membrane uses the above module (or apparatus) shown in FIG. 2. The electric resistance of the membrane can be obtained from the following steps and the equation (12) is used to obtain the product ($\in k_m$). At first, a solution is provided and infiltrates the membrane. The membrane is disposed between two electrodes and the solution is filled between the membrane and each electrode. The relation of current and voltage between the two electrodes twice while the target membrane is installed in between and is not installed is measured and the electric resistance of the membrane is calculated according to Ohm's law.

In one embodiment, the method of having the electroosmotic flow equal to the permeate flow in magnitude but opposite in direction is to adjust the electric field strength to have the permeate flow generated by the mechanical pressure difference stop. In one embodiment, the membrane to be measured is selected from the group consisting of the following: porous membrane such as microfiltration membrane, ultrafiltration membrane, nanofiltration membrane, and ion exchange membrane.

In one embodiment, the method of measuring the streaming potential $\overline{E}$ of the membrane uses a high impedance voltmeter to measure the potential difference across the membrane.

According to another embodiment of the invention, an apparatus 100 for measuring a net charge density of a membrane is disclosed. The apparatus 100 shown in FIG. 3 comprises a membrane permeation measurement module 200, a pressure measurement module 300, a streaming potential measurement module 400, a membrane resistance measurement module 500, and a control module 600. FIG. 4 shows a functional block diagram illustrating an apparatus 100' for measuring a net charge density of a membrane according to another embodiment of the invention. The difference between the apparatus 100 and the apparatus 100' is that the apparatus 100' further comprises an electroosmotic flow measurement module 450. The pressure measurement module 300 measures the mechanical pressure difference between the two surfaces of the membrane to be measured. The streaming potential measurement module 400 measures the streaming potential of the membrane to be measured. The electroosmotic flow measurement module 450 measures the electroosmotic volumetric flow rate of the membrane. The membrane resistance measurement module 500 measures the resistance of the membrane. The control module 600 controls measurement procedures and collects data from each module to calculate the net charge density of the membrane per unit volume. The control module 600 can be for example a computer.

Figure 3:
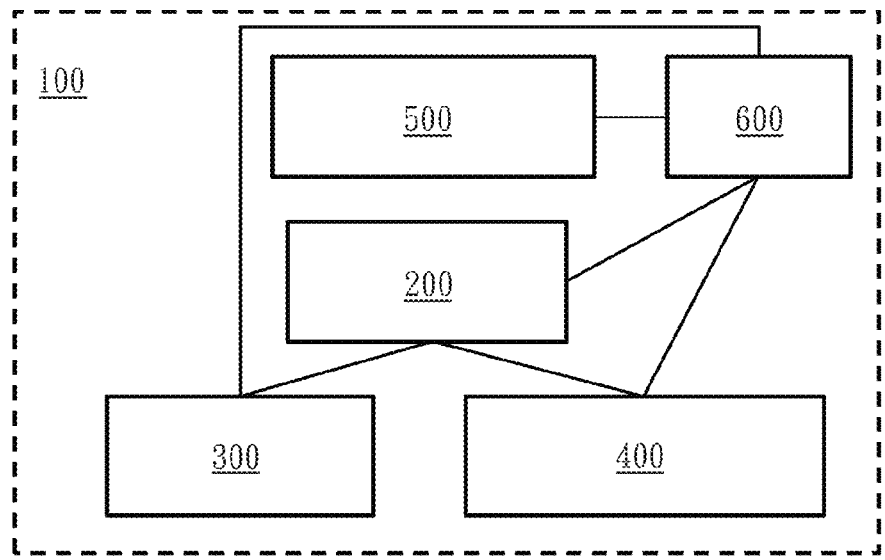
FIG. 3 shows a functional block diagram illustrating an apparatus for measuring a net charge density of a membrane according to one embodiment of the invention.
Figure 4:
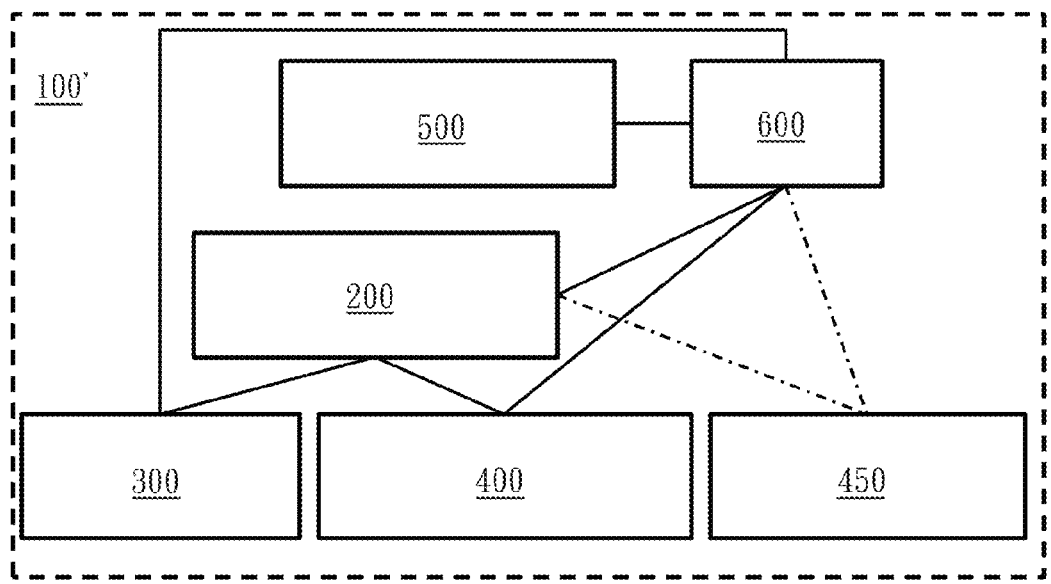
FIG. 4 shows a functional block diagram illustrating an apparatus for measuring a net charge density of a membrane according to another embodiment of the invention.
Figure 5:
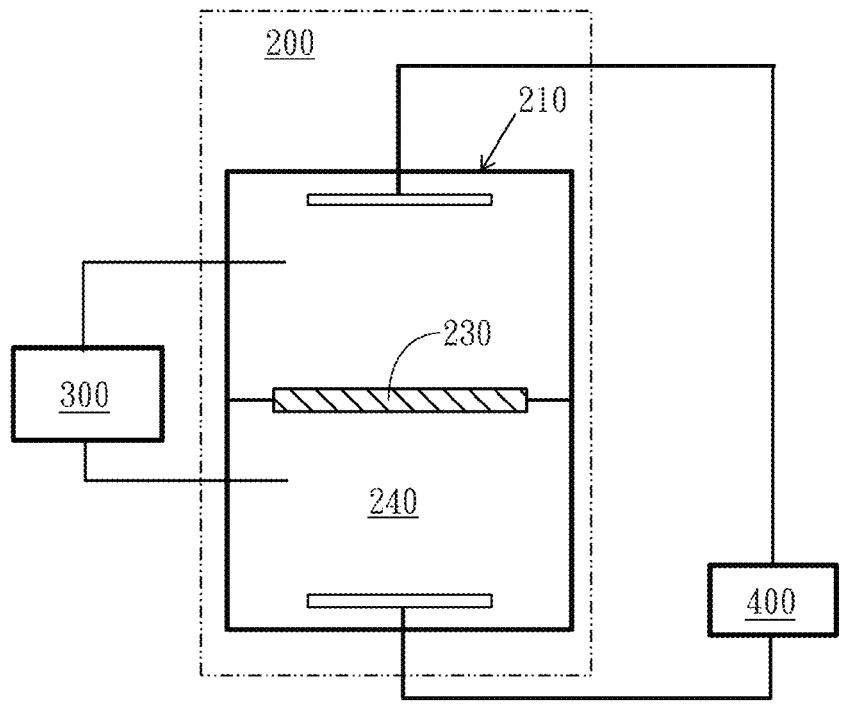
FIG. 5 shows a schematic diagram illustrating the connection of the membrane permeation measurement module 200, the pressure measurement module 300, and the streaming potential measurement module 400 shown in FIG. 3.
Figure 6:
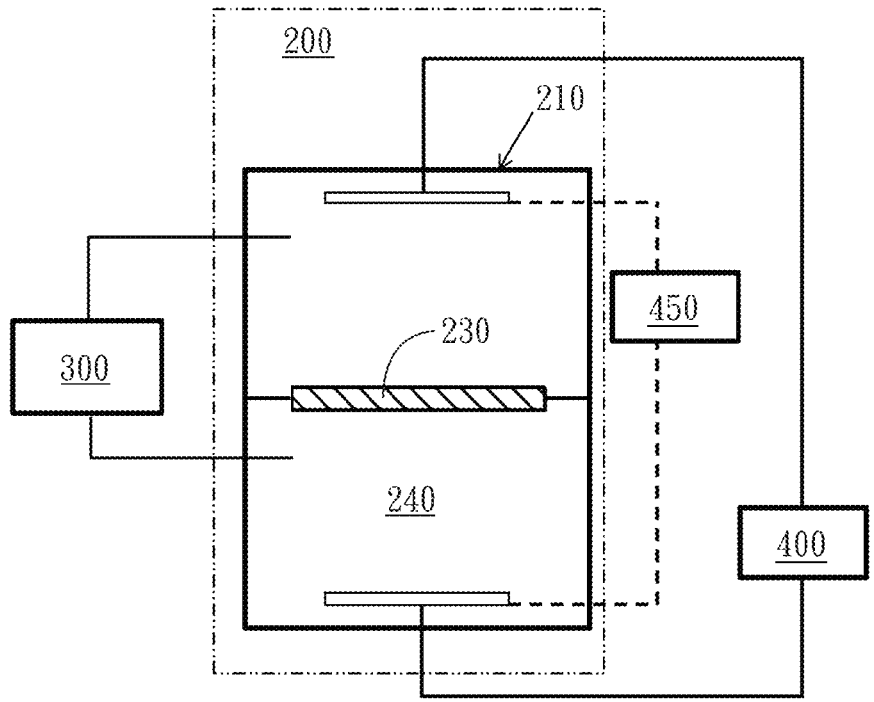
FIG. 6 shows a schematic diagram illustrating the connection of the membrane permeation measurement module 200, the pressure measurement module 300, the streaming potential measurement module 400 and the electroosmotic flow measurement module 450 shown in FIG. 4.

FIG. 5 shows a schematic diagram illustrating the connection of the membrane permeation measurement module 200, the pressure measurement module 300, and the streaming potential measurement module 400 shown in FIG. 3. FIG. 6 shows a schematic diagram illustrating the connection of the membrane permeation measurement module 200, the pressure measurement module 300, the streaming potential measurement module 400 and the electroosmotic flow measurement module 450 shown in FIG. 4. The membrane permeation measurement module 200 comprises a chamber 210, a membrane 230 to be measured, and a solution 240. Besides, the membrane permeation measurement module 200 can further comprise a temperature controller to control the chamber 210 at a fixed temperature (for example, controlling the chamber 210 at 25□); a pump, for transporting the liquid into the chamber; an electronic balance, for measuring a flow quantity of the liquid flowing through the membrane and outputting the flow quantity; and a power supply, electrically coupled to the two electrodes of the membrane permeation measurement module 200.

The pressure measurement module 300 comprise a pressure valve, for controlling and applying a pressure on the two surfaces of the membrane to generate a mechanical pressure difference ΔP between the two surfaces of the membrane; and a pressure sensor, for measuring the mechanical pressure difference ΔP and outputting the mechanical pressure difference ΔP.

The streaming potential measurement module 400 comprises a high impedance voltmeter, for measuring voltage between the two electrodes when the liquid passes through the membrane and outputting the voltage.

The electroosmotic flow measurement module 450 comprises a power supply, two electrodes of which are coupled to the two electrodes of the membrane permeation measurement module 200, and an electronic balance for measuring the electroosmotic flow rate.

The pressure measurement module applies a mechanical pressure difference ΔP on the membrane to generate permeate flow and at the same time the streaming potential measurement module measures the streaming potential. From the relation of the streaming potential and the mechanical pressure difference, the net charge density of the membrane per unit volume can be acquired. If additionally the electroosmotic flow measurement module applies an electric field to generate electroosmotic flow to have the magnitude of the electroosmotic flow equal to the permeate flow but opposite in direction, the net charge density of the membrane per unit volume can be acquired from the relation of the current and the electroosmotic flow.

According to the above embodiment, the net charge density $\rho_E$ of the membrane per unit volume can be acquired according to the relation of the mechanical pressure difference ΔP and the streaming potential $\overline{E}$ by the equation (7): $\rho_E = -(\overline{E}/\Delta P)*(\mu \in k_m/K_p)$ where $\in k_m$ represents the product of the porosity $\in$ and average electrical conductivity $k_m$ of the membrane, μ represents viscosity of the solution, and $K_p$ represents permeability. In addition, the net charge density $\rho_E$ of the membrane per unit volume can be acquired from the equation (9): $\rho_E = -(Q_p/I_a)*(\mu \in k_m/K_p)$ where $\in k_m$ represents the product of the porosity $\in$ and average electrical conductivity $k_m$ of solution in the membrane pore, μ represents viscosity of the solution, $K_p$ represents permeability obtained from the permeate flow, $I_a$ represents the current caused by the electric field, and $Q_p$ represents the volumetric flow rate of the electroosmotic flow.

Figure 7:
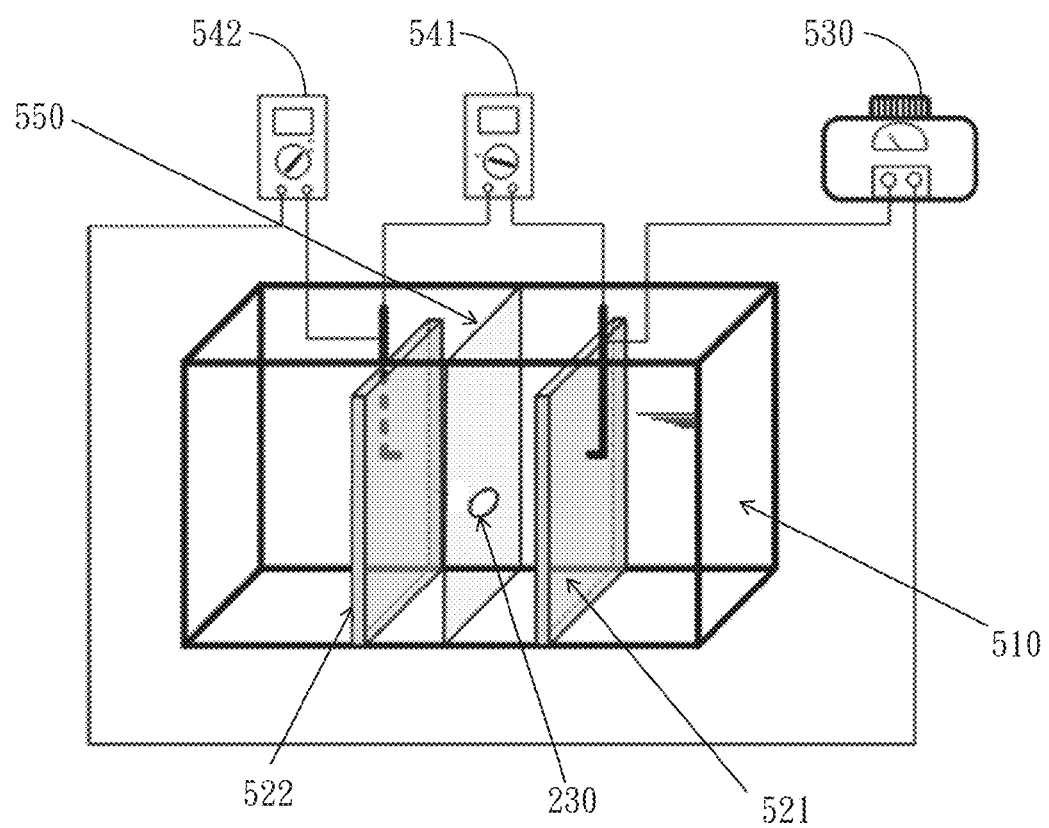
FIG. 7 shows a schematic diagram illustrating a membrane electric resistance measurement module 500 according to one embodiment of the invention.

FIG. 7 shows a schematic diagram illustrating a membrane resistance measurement module 500 according to one embodiment of the invention. The membrane resistance measurement module 500 comprises a membrane resistance measurement container 510, two electrode plates 521, 522, a solution, an AC power supply 530, and two voltmeters 541, 542. The electrode plates 521, 522 are disposed in the membrane electric resistance measurement container 510 and have a specific distance between the two electrode plates 521, 522. The solution is filled in the membrane resistance measurement container. The voltmeter 541 are connected to the electrode plates 521, 522. One contact of the voltmeter 542 is coupled to the AC power supply 530 and the other is coupled to the electrode plate 522. The voltmeter 541, 542 measure voltages and currents. Under a specific voltage, the variation of currents between the two electrodes is measured twice while the membrane is installed in between and is not installed and then the electric resistance of the membrane is calculated from the above relation of current variation based on Ohm's law.

In addition, another embodiment of the invention provides an apparatus for measuring electric resistance of a membrane by having the above membrane resistance measurement module become a stand-alone apparatus.

Moreover, another embodiment of the invention provides a method for measuring electric resistance of a membrane, comprising: providing a solution; having the solution infiltrate the membrane; disposing the membrane between two electrodes and filling the solution between the membrane and each electrode; and measuring the relation of current and voltage between the two electrodes and calculating the resistance of the membrane according to Ohm's law.

In conclusion, the invention discloses a method for measuring a net charge density of a membrane and an apparatus thereof to utilize the applied mechanical pressure difference and the streaming potential of the membrane or the applied electric field and the electroosmotic volumetric flow rate of the electroosmotic flow to acquire the net charge density inside the membrane so that the net charge density per unit volume can be measured effectively to solve the problem in the prior art.

According to the method for measuring electric resistance of a membrane and apparatus thereof, the resistance of a porous membrane such as a microfiltration (MF), ultrafiltration (UF) or nanofiltration (NF) membrane is measured. Furthermore, if the porosity of the membrane is known to be $\in$ (for example, when a membrane has large pores, the porosity $\in$ can be obtained from other methods), the average electrical conductivity $k_m$ of solution in the membrane pore can be acquired according to the method and apparatus for measuring electric resistance of a membrane disclosed by the invention. On the other hand, if the average electrical conductivity $k_m$ of the membrane is known, the porosity $\in$ can be acquired according to the method and apparatus for measuring electric resistance of a membrane disclosed by the invention.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An apparatus for measuring a net charge density of a membrane, comprising:

a membrane permeation measurement module, comprising a chamber, two electrodes disposed in the chamber, a target membrane to be measured, and a solution, for measuring permeation rate caused by a pressure difference ΔP between two surfaces of the target membrane and electroosmotic volumetric flow rate caused by an electric field applying across the target membrane;

a pressure measurement module, for measuring the mechanical pressure difference ΔP between the two surfaces of the target membrane; and a streaming potential measurement module, for measuring the streaming potential $\overline{E}$ across the target membrane; and a control module, for controlling measurement procedures and collecting data from each module to calculate the net charge density $\rho_E$ of the target membrane per unit volume according to the relation of the mechanical pressure difference ΔP and the streaming potential $\overline{E}$, by the following equation (7):

$$\rho_E = -(\overline{E}/\Delta P)*(\mu \in k_m/K_p) \qquad (7)$$

where $\in k_m$ represents the product of the porosity $\in$ and average electrical conductivity $k_m$ of the target membrane, μ represents viscosity of the solution, and $K_p$ represents permeability; and wherein the product of the porosity $\in$ and average electrical conductivity $k_m$ of the target membrane is acquired by measuring electric resistance of the target membrane.

2. The apparatus according to claim 1, further comprising:
a membrane electric resistance measurement module, for measuring resistance of the target membrane.

3. The apparatus according to claim 1, wherein the membrane permeation measurement module further comprises:
a temperature controller, for controlling the chamber at a fixed temperature;
a pump, for transporting the solution into the chamber;
an electronic balance, for measuring a flow quantity of the solution flowing through the target membrane and outputting the flow quantity; and
a power supply, electrically coupled to the two electrodes of the membrane permeation measurement module.

4. The apparatus according to claim 1, wherein the pressure measurement module comprises:
a pressure valve, for controlling and applying a pressure on the two surfaces of the target membrane to generate a mechanical pressure difference $\Delta P$ across the target membrane; and
a pressure sensor, for measuring the mechanical pressure difference $\Delta P$ and outputting the mechanical pressure difference $\Delta P$.

5. The apparatus according to claim 1, wherein the streaming potential measurement module comprises:
a high impedance voltmeter, for measuring voltage between the two electrodes when the solution passes through the target membrane and outputting the voltage.

6. The apparatus according to claim 1, wherein the membrane electric resistance measurement module comprises:
a membrane resistance measurement container;
two electrode plates, disposed in the membrane resistance measurement container and having a specific distance between the two electrode plates;
a solution, filled in the membrane resistance measurement container;
an AC power supply, for supplying power between the two electrode plates;
two voltmeters, one of which is electrically coupled to the two electrode plates and the other of which has one end electrically coupled to the AC power supply and has the other end electrically coupled to one of the two electrode plates to measure voltages and currents;

wherein under a specific voltage the variation of currents between the two electrodes is measured while the target membrane is installed in between or is not installed and then the resistance of the target membrane is calculated from the above relation of current variation based on Ohm's law.

7. An apparatus for measuring resistance of a membrane, comprising:
a membrane resistance measurement container;
two plate-electrodes, disposed in the membrane resistance measurement cell and having a specific distance between the two electrode plates;
a solution, filled in the membrane resistance measurement cell;
an AC power supply, for supplying power between the two electrode plates;
two voltmeters, one of which is electrically coupled to the two electrode plates and the other of which has one end electrically coupled to the AC power supply and has the other end electrically coupled to one of the two electrode plates to measure voltages and currents; and
a control module, for controlling measurement procedures and collecting data from each module to calculate the net charge density $\rho_E$ of the target membrane per unit volume according to the relation of the mechanical pressure difference $\Delta P$ and the streaming potential $\overline{E}$, by the following equation (7):

$$\rho_E = -(\overline{E}/\Delta P)*(\mu \in k_m/K_p) \qquad (7)$$

where $\in k_m$ represents the product of the porosity $\in$ and average electrical conductivity $k_m$ of the target membrane, $\mu$ represents viscosity of the solution, and $K_p$ represents permeability; and
wherein the product of the porosity $\in$ and average electrical conductivity $k_m$ of the target membrane is acquired by measuring electric resistance of the target membrane, and
wherein under a specific voltage the variation of currents between the two electrodes is measured while the target membrane is installed in between or is not installed and then the resistance of the target membrane is calculated from the above relation of current variation based on Ohm's law.

* * * * *